United States Patent [19]

Arima et al.

[11] 4,001,589
[45] Jan. 4, 1977

[54] RADIOMETRIC ANALYZER WITH PLURAL RADIATION SOURCES AND DETECTORS

[75] Inventors: Sumitaro Arima, Sendai; Minoru Oda, Amagasaki; Kyoichi Miyashita, Amagasaki; Mamoru Takada, Amagasaki, all of Japan

[73] Assignees: Tohoku Electric Power Company, Inc.; Mitsubishi Denki Kabushiki Kaisha, both of Tokyo, Japan

[22] Filed: Apr. 17, 1975

[21] Appl. No.: 569,143

Related U.S. Application Data

[63] Continuation of Ser. No. 432,235, Jan. 10, 1974.

[52] U.S. Cl. .............................. 250/336; 250/358 R
[51] Int. Cl.² .......................................... G01T 1/16
[58] Field of Search .......... 250/253, 269, 336, 364, 250/428, 432, 435, 358

[56] References Cited

UNITED STATES PATENTS 3,622,795   11/1971   Dorman, Jr. et al. ......... 250/432 X Primary Examiner—Davis L. Willis
Attorney, Agent, or Firm—Oblon, Fisher, Spivak, McClelland & Maier

[57] ABSTRACT

A radiometric analyzer for measuring characteristics of a material by radiation comprises a plurality of systems in which each consists of a radiation source and a radiation detector which are the same in number as the number of elements of the molecule of the material and a linear calibration circuit having inverse response characteristics (calibration curve) of the respective systems of detectors, whereby the measurement is carried out by a four fundamental rules operation of the mutual outputs of said detector system obtained through said linear calibration circuit. One typical embodiment is a radiometric analyzer for hydrocarbons which measures the density of heavy oil, the sulfur content and the calorific value by three detector systems which include a $\gamma$-ray source ($E_\gamma > 50$ KeV), a soft X-ray source ($E_x \doteq 20$ Kev), and a neutron ray source.

2 Claims, 6 Drawing Figures

RADIOMETRIC ANALYZER WITH PLURAL RADIATION SOURCES AND DETECTORS

This is a continuation of application Ser. No. 432,235 filed Jan. 10, 1974.

BACKGROUND OF THE INVENTION

1. Field of the Invention

This invention relates to a radiometric analyzer for precisely measuring various characteristics of a material, e.g. a hydrocarbon, under rational automatic calibration to the change of formula of the material in an analyzer for measuring various characteristics of the material with radiation.

2. Description of the Prior Art

Analyzers for measuring various characteristics of a material by radiation techniques are known in the art. However, by and large, such analyzers have not measured the precise physical characteristics of the material, but rather have measured approximate values.

In order to measure more precisely the characteristics of a material, it is necessary to compensate the measured values depending upon the change of formula of the material. The compensation of the formulation of a material may be, for example, a compensation by the ratio of carbon to hydrogen for a measurement of the density of a hydrocarbon. In order to measure the density of a hydrocarbon, the number of atoms of carbon and hydrogen in a unit of volume are respectively multiplied by a weighing factor which is the ratio of the mass numbers (12 : 1) and are then added together. However, when a γ-ray density meter is used, the weighing factor is not the ratio of the mass numbers, but is approximately the ratio of the atomic numbers (6 : 1), so that the correspondence of the measured value of the density will not be accurate.

Heretofore, as a compensation of the measured values, the hydrogen density and the ratio of carbon to hydrogen atoms have been separately measured and the compensation has been introduced by a desirable calibration coefficient as a result of experiments. However, it has been difficult to determine precisely the compensation function required by such conventional methods due to requirements of greater accuracy.

Additionally, when multiple compensations are yielded by using parallel systems for detection, the calibrations are very complicated so as to make it difficult to determine the required operations including the relationships of the response functions of each detective system in automatic operations. Also, the physical meaning of the operated output becomes unclear and a presumption of residual error exists.

SUMMARY OF THE INVENTION

It is a primary object of the present invention to provide a new and unique compensation system for overcoming the foregoing difficulties.

The foregoing and other objects are attained in accordance with one aspect of the present invention based on the relationships that an output of a radiation detector is a function of the addition of certain multipled values (i.e., the number of atoms of molecule of material per unit volume times the specific weight of the source-detector for respective atoms), and that all of the characteristics measurable by a radiometric analyzer can be calculated by suitable operations between the measured values by using systems of the radiation source-detector which are the same in number as the number of elements of molecule in the material.

The basic structure of the analyzer of the present invention is as follows. In the radiometric analyzer for measuring various characteristics of the material by using radioactive rays, a number of systems are provided which comprise the radiation source and the radiation detector having different response functions which are the same in number as the number of elements of molecule of the material. Linear calibration circuits having inverse characteristic response functions to those of the respective systems of detectors are also provided whereby the measurement is carried out by a four fundamental rules operation of the mutual outputs of said detector systems obtained through said linear calibration circuits. The radiometric analyzer of the present invention having the foregoing basic structure can be used for the measurement of various materials.

As one preferred embodiment, a radiometric analyzer for hydrocarbons is disclosed which comprises a γ-ray detector for detecting γ-rays passed through a sample, a first logarithmic amplifier to linearize the output of the γ-ray detector, an X-ray detector for detecting X-rays passed through the sample, a second logarithmic amplifier to linearize the output of the X-ray detector, a neutron detector for detecting the neutrons scattered in the sample, an intercept lineation amplifier to linearize the outputs of the neutron detector, and a four fundamental rules operator for operating by four fundamental rules on the outputs of said first logarithmic amplifier, said second logarithmic amplifier and said intercept lineation amplifier. By the foregoing, at least one of the contents of carbon, hydrogen or sulfur of the sulfur-containing hydrocarbon per unit of volume or unit of weight or a value derived by the four fundamental rules operation of the contents may be measured.

The radiometric analyzer of the present invention indirectly measures the calorific value of hydrocarbons from a calculation of the contents of the elements of the molecules of the hydrocarbon, since we have found that the optimum indication of the calorific value of a hydrocarbon is a primary combination of the desirable rate of contents of carbon, hydrogen and sulfur.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

Figure 1:
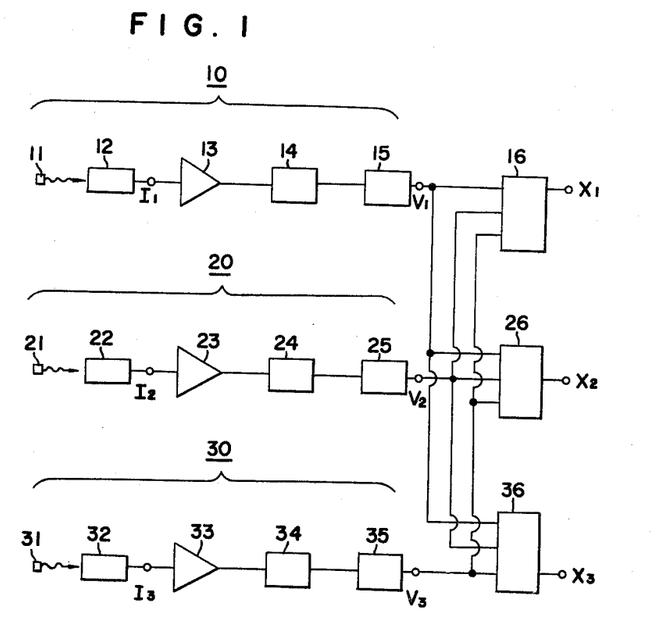
FIG. 1 is a block diagram showing the principles of operation of a preferred embodiment of the apparatus according to the present invention.

$$X_1 = \frac{1}{\Delta}\left[\left(\frac{a_{22}a_{33} - a_{32}a_{23}}{K_1}\right) \times V_1 - \left(\frac{a_{12}a_{33} - a_{32}a_{13}}{K_2}\right) \times V_2 + \left(\frac{a_{12}a_{23} - a_{22}a_{13}}{K_3}\right) \times V_3\right] \quad (7)$$

$$X_2 = \frac{1}{\Delta}\left[\left(\frac{a_{21}a_{33} - a_{31}a_{23}}{K_1}\right) \times V_1 + \left(\frac{a_{11}a_{33} - a_{31}a_{13}}{K_2}\right) \times V_2 + \left(\frac{a_{11}a_{23} - a_{21}a_{13}}{K_3}\right) \times V_3\right] \quad (8)$$

$$X_3 = \frac{1}{\Delta}\left[\left(\frac{a_{21}a_{32} - a_{31}a_{22}}{K_1}\right) \times V_1 - \left(\frac{a_{11}a_{32} - a_{31}a_{12}}{K_2}\right) \times V_2 + \left(\frac{a_{11}a_{22} - a_{21}a_{12}}{K_3}\right) \times V_3\right] \quad (9)$$

DETAILED DESCRIPTION OF THE PREFERRED EMBODIMENTS

Referring now to the drawings, wherein like reference numerals designate identical or corresponding parts throughout the several views, and more particularly to FIG. 1 thereof, there is shown a block diagram illustrative of the principles of operation of the radiometric analyzer of the present invention wherein the elements in the materials to be measured are provided in three types. The apparatus is seen to comprise first, second and third detector systems 10, 20 and 30, radiation sources 11, 21 and 31 radiation detectors 12, 22 and 32, amplifiers 13, 23 and 33, counting rate meters 14, 24 and 34, linear calibration circuits 15, 25 and 35, and four fundamental rules operators 16, 26 and 36. The combination of the radiation sources 11, 21 or 31 with their respective detectors 12, 22 or 32 are selected so as to yield different response functions to the measured materials.

Figure 2:
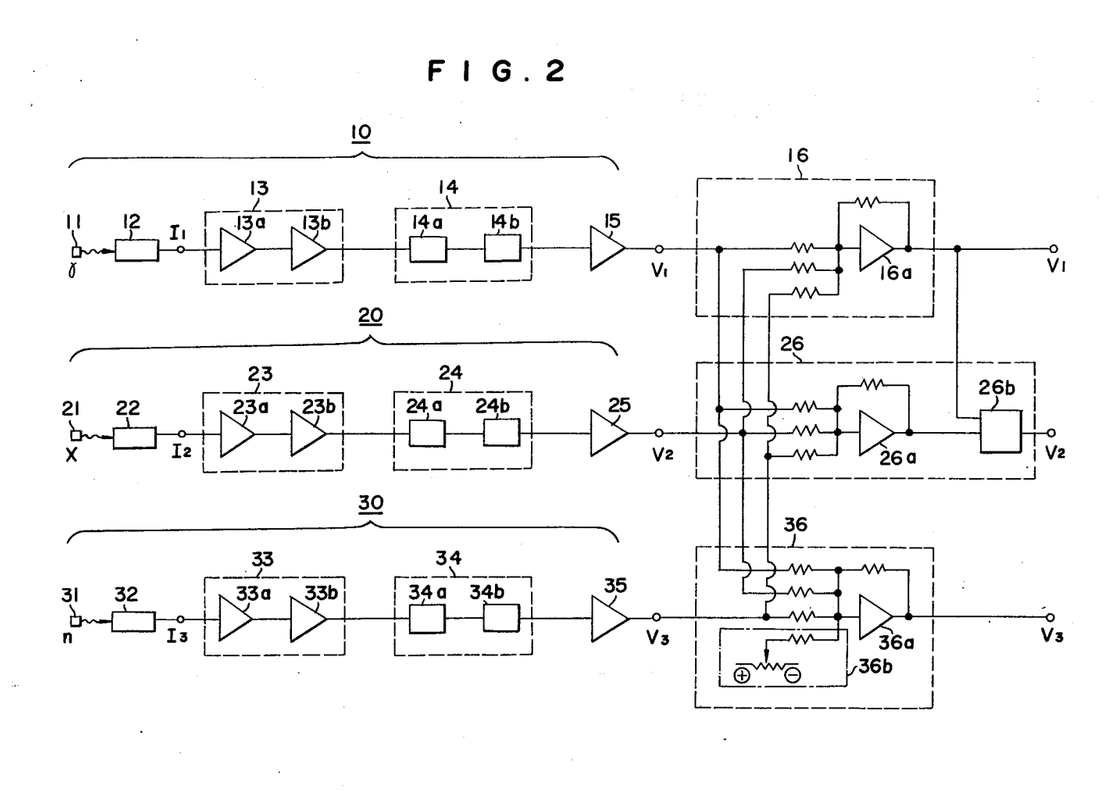
FIG. 2 is a block diagram showing a preferred embodiment of a radiometric analyzer used for hydrocarbon analysis according to the present invention.

The masses of the three types of elements of the measured materials per unit volume are shown as $X_1$, $X_2$ and $X_3$ (mass/volume, which is given as W/V dimensionally), and the output pulse counting rate of the detectors 12, 22 and 32 of the three systems are respectively shown as $I_1$, $I_2$ and $I_3$. Generally, their relationships are given by the following equations:

$$I_1 = f_1(a_{11}X_1 + a_{12}X_2 + a_{13}X_3), \quad (1)$$
$$I_2 = f_2(a_{21}X_1 + a_{22}X_2 + a_{23}X_3), \quad (2)$$

and $$I_3 = f_3(a_{31}X_1 + a_{32}X_2 + a_{33}X_3), \quad (3)$$

wherein $f_1$, $f_2$ and $f_3$ represent the response functions respectively of the three systems, and $a_{11}$, $a_{12}$, ... $a_{33}$ represent constants determined by the radiation sources and detectors of the systems. These relationships are illustrated in a particular case as shown in FIG. 2.

The linear calibration circuits 15, 25 and 35 have inverse functional characteristics of the functions $f_1$, $f_2$ and $f_3$. The functions $f_1$, $f_2$ and $f_3$ are reduced to linear combinations of $X_1$, $X_2$ and $X_3$ so as to give the respective outputs $V_1$, $V_2$ and $V_3$ as follows:

$$V_1 = K_1(a_{11}X_1 + a_{12}X_2 + a_{13}X_3), \quad (4)$$

$$V_2 = K_2(a_{21}X_1 + a_{22}X_2 + a_{23}X_3), \quad (5)$$

and $$V_3 = K_3(a_{31}X_1 + a_{32}X_2 + a_{33}X_3), \quad (6)$$

wherein $K_1$, $K_2$ and $K_3$ represent arbitrary gain factors determined by the particular apparatus. The masses $X_1$, $X_2$ and $X_3$ of the three elements per unit volume can be given by the four fundamental rules operators 16, 26 and 36 as follows:

wherein $$\Delta = \begin{vmatrix} a_{11} & a_{12} & a_{13} \\ a_{21} & a_{22} & a_{23} \\ a_{31} & a_{32} & a_{33} \end{vmatrix} \quad (10)$$

In the foregoing, the masses $X_1$, $X_2$ and $X_3$ (W/V) of the elements per unit volume were calculated by the four fundamental rules operators 16, 26 and 36. When the four fundamental rules operations are thereby performed, the density of the measured material [$\rho = X_1 + X_2 + X_3$ (W/V)], the contents of a specific element [$X_1(W/V) / \rho (W/V)$] and the ratio of elements of the materials [$X_1 : X_2 : X_3$] can be calculated.

In accordance with the system of measurement of the present invention, the calibrating function can be simplified so that the values can be calculated by the four fundamental rules operation. By said operation, calculated values which clearly correspond to the normal physical values (confirmed values) can be given.

In accordance with the system of the present invention, various features of the response functions (calibration curve) of the detector system can be eliminated at the linear calibration circuit (inverse function generator) so that the mode of operation between the outputs of the detector systems is relatively and advantageously uncomplicated.

A radiometric analyzer for hydrocarbon analysis according to the invention will now be illustrated in detail with reference to FIG. 2. The analyzer therein depicted measures the density, sulfur content, and calorific value of heavy oil, which is a sulfur containing hydrocarbon. The density and sulfur content can be precisely measured by the radiometric method but the calorific value (per unit of weight) is indirectly measured from the ratio of elements of the material.

In the first detector system 10 of FIG. 2, the reference numeral 11 designates a γ-ray source, and 12 designates a γ-ray detector, e.g. a proportional counter for γ-ray measurement. In the second detector system 20, the reference numeral 21 designates an X-ray source, and 22 designates an X-ray detector, e.g. a proportional counter for X-ray measurement. In the third detector system 30, the reference numeral 31 designates a neutron source and 32 designates a thermal neutron detector, e.g. a $BF_3$ counter.

The first detector system 10 provides an output signal which is substantially proportional to the density since the mass absorption coefficient of γ-rays having higher than several tens of KeV of energy is substantially constant independent of the absorption material. As examples of suitable γ-ray sources, $^{241}Am$ (60 KeV), $^{137}$Cs(662 KeV), or the like, can be used. The absorption coefficients of atoms of the material are not always equal. Accordingly, it is difficult to precisely determine the density by using only the first detector system 10, and hence it becomes necessary to provide the compensation operation using the output signal of the other detector system.

The second detector system 20 provides an output signal which is substantially proportional to the sulfur content per unit of volume by using the absorption of X-rays having about several KeV, e.g. 20 KeV of energy. For example, the mass absorption coefficient of sulfur exposed to X-rays having about 17 KeV is about 20 times that of other elements, so that the output of such a detector system is especially sensitive to sulfur. As an example of suitable X-ray source, $^{241}$Am (17 KeV) can be used. In the system, it becomes necessary to provide the compensation operation by using the output signal of the other detector system, the same as in the density case explained above.

The third detector system 30 provides a signal which is substantially proportional to the hydrogen content per unit of volume by using the scattering and slowing of high speed neutrons. Hydrogen has substantially the same mass as that of neutrons, so that the slowing effect achieved by elastic scattering is particularly high, without being effected by the other elements. As the neutron source, $^{241}$Am-Be or Ra-Be, for example, may be used.

Referring once more to the first system 10, it is seen to comprise an amplifier 13, consisting of a pre-amplifier 13a and a main-amplifier 13b, a counting rate meter 14 consisting of a peak detector 14a and a counting rate meter 14b a logarithmic amplifier 15 operating as a linear calibration amplifier, and four fundamental rules operator 16 which includes a mixer amplifier 16a.

The second system 20 comprises an amplifier 23 consisting of a pre-amplifier 23a and a main-amplifier 23b, a counting rate meter 24 consisting of a peak detector 24a and a counting rate meter 24b, a logarithmic amplifier 25 operating as a linear calibration amplifier, and a four fundamental rules operator 26 which includes a mixer amplifier 26a and a divider 26b.

The third system 30 is seen to similarly comprise an amplifier 33 including a pre-amplifier 33a and a main-amplifier 33b, a counting rate meter 34 which consists of a peak detector 34a and a counting rate meter 34b, an addition linear amplifier 35 (level amplifier) operating as a calibration amplifier, and a four fundamental rules operator 36 which includes a mixer amplifier 36a and a constant member addition circuit 36b.

The peak detectors 14a and 34a of the first and third systems 10 and 30 comprise conventional discriminators. However, the peak detector 24a of the second system 20 comprises a single channel pulse height analyzer. When $^{241}$Am is used, only a pulse based on X-rays having 17 KeV will be encountered.

If the elements of heavy oil are presumed to comprise components of carbon, hydrogen, and sulfur, and the masses of carbon, hydrogen and sulfur per unit of volume are represented as C, H, S (W/V), the pulse counting rate of each detector system can be mathematically represented as follows:

$$I_1 = I_{01} \exp\{-(\mu_C C + \mu_S S + \mu_H H) d_1\} \quad (11)$$
$$I_2 = I_{02} \exp\{-(\mu'_C C + \mu'_S S + \mu'_H H) d_2\} \quad (12)$$

$$I_3 = \alpha C + \beta S + \gamma H + \delta \quad (13)$$

wherein $I_{01}$ and $I_{02}$ represent the counting rates of the respective measurement systems when oil samples are empty, $\mu_C$, $\mu_S$ and $\mu_H$ represent mass absorption coefficients of carbon, sulfur and hydrogen respectively, and $d_1$ and $d_2$ represent the thickness (g/cm$^2$) of the sample. The values of $\alpha$, $\beta$ and $\delta$ are constants which depend upon the analyzer. The respective pulse signals are converted to a voltage proportional to the counting rate by the counting rate meters 14, 24 and 34, respectively.

The following linear calibrated voltages are provided by the logarithmic amplifiers 15 and 25 based on the pulse counting rates I$_1$ and I$_2$ and by the intercept additional linear amplifier 35 based on the pulse counting rate I$_3$, respectively:

$$V_1 = K_1(\mu_C C + \mu_S S + \mu_H H) \quad (14)$$

$$V_2 = K_2(\mu'_C C + \mu'_S S + \mu'_H H) \quad (15)$$
$$V_3 = K_3(\alpha C + \beta S + \gamma H), \quad (16)$$

wherein $K_1$, $K_2$ and $K_3$ are arbitrary gain factors depending upon the particular apparatus.

In equation 14, V$_1$ is a voltage which is substantially proportional to the density, since the values $\mu$C, $\mu$S and $\mu$H are substantially the same. In equation 15, V$_2$ is a voltage which is substantially proportional to the sulfur content, since the value of $\mu'_S$ is markedly higher than $\mu'_C$ and $\mu'_H$.

However, the above relationships are only an approximation, and accordingly a voltage which is precisely proportional to the object value may be calculated by the four fundamental rules operators. In the four fundamental rules operators 16, 26 and 36, the following calculations are provided:

$$V'_1 = K'_1(b_{11}V_1 + b_{12}V_2 + b_{13}V_3) \quad (17)$$

$$V'_2 = K_2' \left(\frac{b_{21}V_2 + b_{22}V_2 + b_{23}V_3}{V_1'}\right) \quad (18)$$

$$V'_3 = K'_3(b_{31}V_1 + b_{32}V_2 + b_{33}V_3 + b_o), \quad (19)$$

wherein $K'_1$, $K'_2$, $K'_3$ are constants, $b_{11}$, $b_{12}$ ... $b_{33}$ and $b_o$ are determined to give the following equations based on equations (14), (15) and (16).

Accordingly, the final output voltages can be represented as follows:

$$V'_1 = K''_1(C + S + H) = K''_1 \rho \ (\rho = \text{density}) \quad (20)$$
$$V'_2 = K''_2 S/(C = S + H) = K''_2 S/\rho \ (S/\rho = \text{sulfur content}) \quad (21)$$
$$V'_3 = K''_3(k + lC + mS + nH) = K''_3 Q \ (Q = \text{calorific value}), \quad (22)$$

wherein K''$_1$, K''$_2$ and K''$_3$ are constants depending upon the apparatus.

The constants $k$, $l$, $m$, and $n$ of equation (22) are determined so as to provide maximum correlation with the calorific value. For example, the ranges of $k$, $l$, $m$ and $n$ which provide the desirable correlation with respect to the instant example are:

$10,000 < k < 15,000$; $-5,000 < l < -3,000$; $-10,000 < m < -5,000$ and $3,000 < n < 8,000$.

As stated above, in accordance with the system of the present invention, a compensation function necessary for an increase in required accuracy can be precisely determined whereby measured values having extremely high accuracy can be provided. The physical meaning (dimensions) of the operation outputs is also clear.

The system according to the present invention requires measuring systems which are the same in number as the number of elements of the heavy oil (carbon, hydrogen and sulfur) with respect to each value measured. However, it is unnecessary to provide more measuring systems than those values to be measured. Accordingly, the system of the invention in calculating three values of a density, a sulfur content and a calorific value from three measuring systems can be quite economical.

The calorific value of heavy oil can be measured from a density $[\rho(w/v)]$, a hydrogen content $[H(W/V)]$ per unit of volume, or a hydrogen content $[H(W/V) / \rho (W/V)]$ per unit of weight. However, it has been found that the system of the present invention is superior than such conventional methods.

In the foregoing embodiments, the radiation is detected in a digital manner and the four fundamental rules operation is carried out in an analogue manner. However, a digital technique and an analogue technique can be applied to the detection of the radiation and the four fundamental rules operation. In the analogue technique, it may be modified to decrease drift mutually by applying bias.

The advantages of the analyzer of the present invention can also be provided by replacing a portion of the plurality of detecting systems connected to a certain detector other than a radiation detector.

Figure 3:
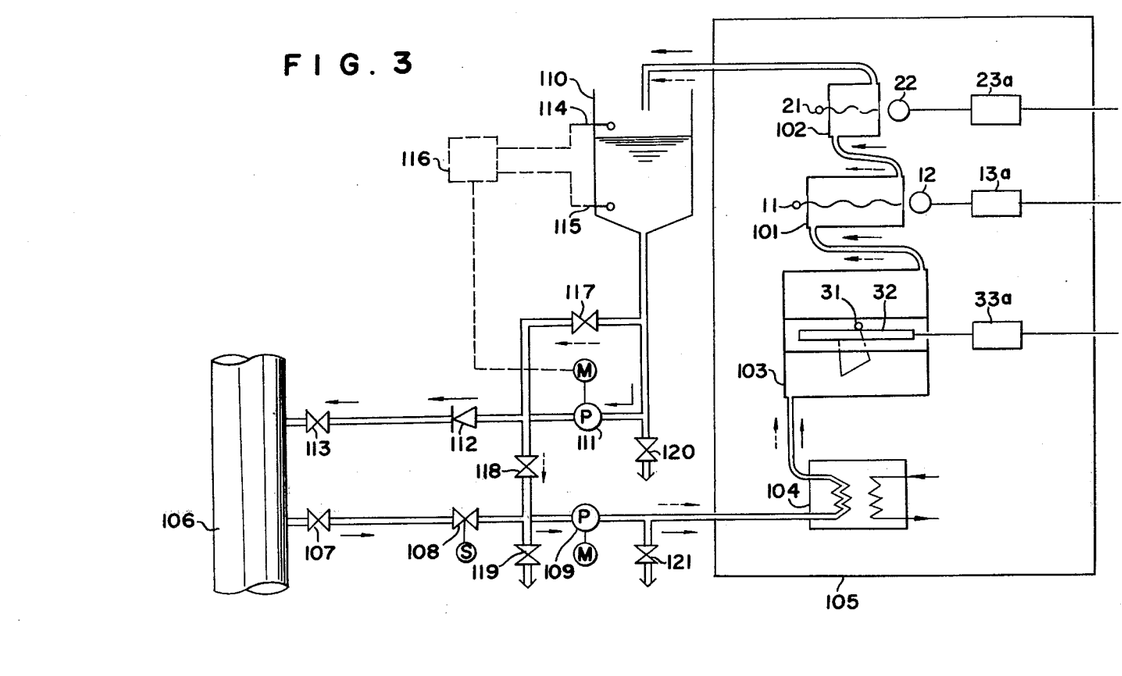
FIG. 3 is a schematic view showing an enlarged part of a sample vessel and other related parts of the radioactive analyzer used for hydrocarbon analysis according to the present invention.

FIG. 3 is a schematic view of sample vessel and related parts of a radioactive analyzer for hydrocarbon analysis according to the present invention. In the embodiment therein depicted, it is possible to use an on-line measurement for continuously measuring the heavy oil passing through a pipe and to use a batch measurement for measuring each sample of heavy oil. Referring specifically to FIG. 3, the reference numeral 101 designates a sample vessel for γ-ray measurements, 11 designates a $^{241}$Am - γ -ray source, 12 designates a γ-ray detector, 13a designates a pre-amplifier, 102 designates a sample vessel for X-ray measurements, 21 designates a $^{241}$Am - X-ray source, 22 designates an X-ray detector, 23a designates a pre-amplifier, 103 designates a sample vessel for neutron measurement, 31 designates a $^{241}$Am-Be neutron source, 32 designates a neutron detector, 33a designates a pre-amplifier, and 104 designates a heat-exchanger which is equipped for heating the heavy oil fed into the sample vessel to a predetermined temperature so as to eliminate the necessity of calibrating the temperature fluctuation and to maintain a stable measurement.

The above-described parts are maintained in a constant temperature case 105 which is kept at a temperature the same as that of the heated heavy oil temperature, e.g. 50° C, so as to maintain the stability of the radiometric analyzer. The flow of the heavy oil during the measurement of the heavy oil passing through a heavy oil pipe 106 in the on-line system is indicated by the solid arrows in FIG. 3. The heavy oil sample in the pipe 106 is passed through a valve 107, an electromagnetic valve 108, a constant flow pump 109, the heat-exchanger 104 and is radiometrically measured in the sample vessels 103, 101 and 102. The heavy oil sample is then fed to the storage tank 110 at atmospheric pressure. Thereafter, the heavy oil sample is fed by a pump 111 through a check valve 112 and a valve 113 back to the pipe 106. The operation of the pump 111 is controlled by a controller 116 according to the signals of conventional level detectors 114 and 115.

The flow of heavy oil during the measurement of the sampled heavy oil by the batch technique is indicated by the broken arrows in FIG. 3. The heavy oil sample is fed to the storage tank 110 and is passed through the valves 117 and 118, a constant flow pump 109, and heat-exchanger 104 to the sample vessels 103, 101 and 102 and is returned to the storage tank 110. Valves 119, 120 and 121 are used for discharging the heavy oil sample after the measurement. Thus, the density, the sulfur content, and calorific value of the heavy oil sample are measured by the analyzer shown in FIGS. 2 and 3. The measured values from the analyzer of the present invention are compared with the measured values according to the analysis of the Japanese Industrial Standard wherein the density is measured by the hydrometer I method; the sulfur content is measured by the quartz tube-oxygen method; and the calorific value is measured by a B-type calorimeter.

Figure 4:
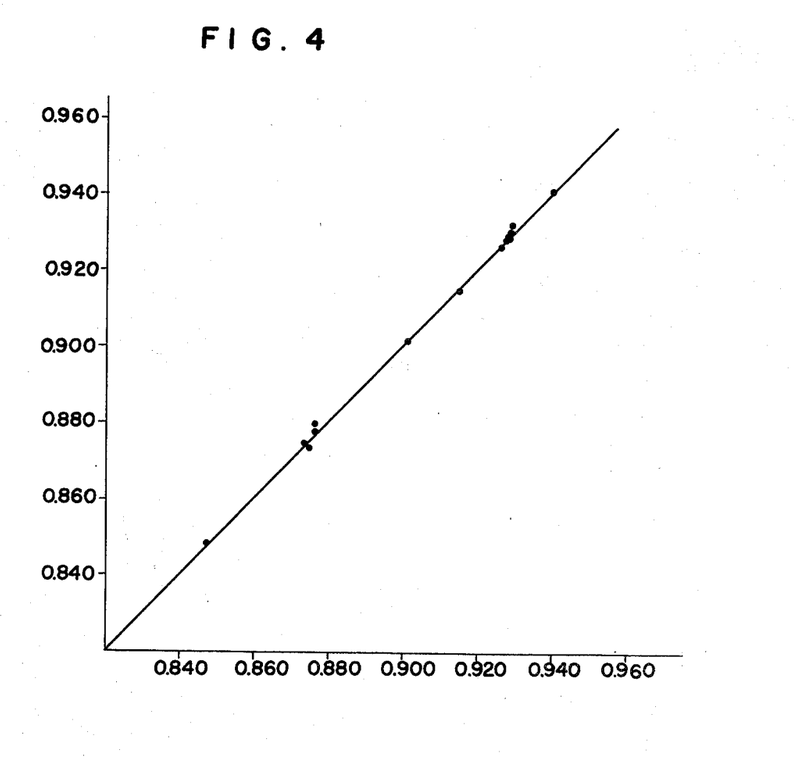
FIGS. 4, 5 and 6 are graphs showing the mutual relationships of the density, the content of sulfur, and the calorific value of heavy oil to values as measured by the Japanese Industrial Standard.
Figure 5:
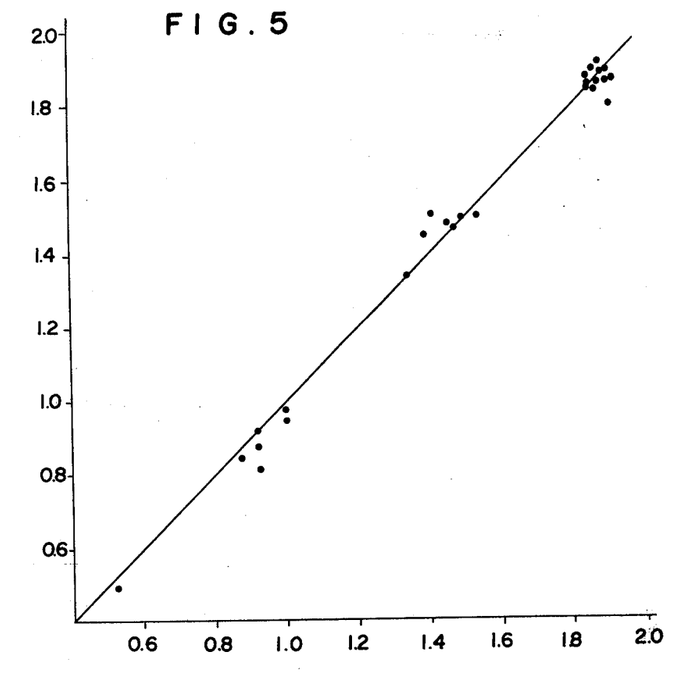
Figure 6:
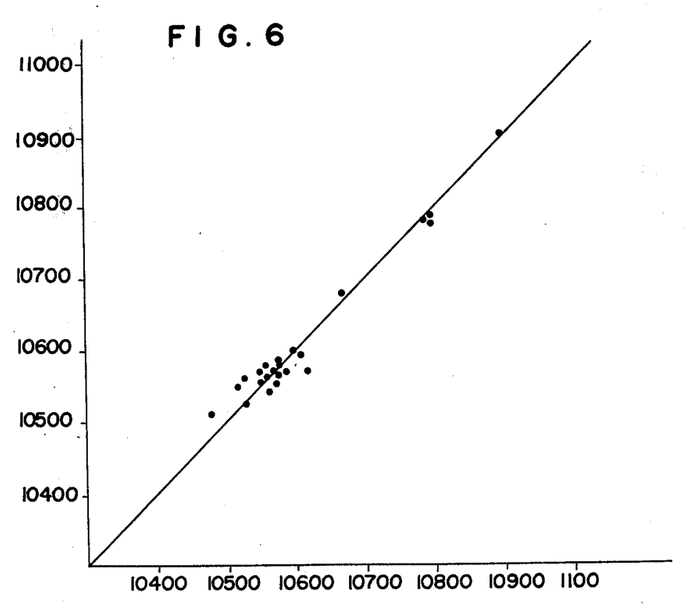

FIGS. 4, 5 and 6 show measured results of the density, sulfur content and calorific value of about 30 types of heavy oils, wherein the measured values from the analyzer of the invention are seen to be well correlated with the measured values by direct analysis, and wherein the standard deviations between the 2 techniques are respectively 0.0008 (g/cm$^3$), 0.029 (%), and 17 (Kcal/kg).

It is clear from the foregoing that precise measurements are provided by the analyzer of the present invention. In the Japanese Industrial Standard, the allowable error of sulfur content measured by the same apparatus and the same person is 0.12 (%). Accordingly, the accuracy of the analyzer of the present invention is quite high. The accuracy can be further increased by improving the measuring system.

In the foregoing embodiment, the measurement of the characteristics of heavy oil have been illustrated. However, the fundamental features of the invention can be applied to the measurement of hydrocarbons and other various solid and liquid materials, as well as heavy oil.

As stated in detail above, the present invention measures various characteristics of a material with high accuracy to a rational calibration system to change of formula of the material in the radiometric analyzer.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A radiometric analyzer for measuring the masses per unit volume X1, X2, and X3 of a material by radiation comprising:
    a first radiation source for bombarding the material with a first radiation;
    a first radiation detector for receiving the first radiation after bombardment with respect to the material;
    a second radiation source for bombarding the material with a second radiation;
    a second radiation detector for receiving the second radiation after bombardment with respect to the material;

a third radiation source for bombarding the material with a third radiation;
a third radiation detector for receiving the third radiation after bombardment;
a first linear calibration circuit connected to receive the output of the first radiation detector for generating an output signal V1;
a second linear calibration circuit connected to receive the output of the second radiation detector for generating an output signal V2;
a third linear calibration circuit connected to receive the output of the third radiation detector for generating an output signal V3;
a first four fundamental rules operator for generating an output indicative of X1;
a second four fundamental rules operator for generating an output indicative of X2;
a third four fundamental rules operator for generating an output indicator of X3;
means connecting the output signal V1 of the first linear calibration circuit to the inputs of the first, second and third four fundamental rules operators;
means connecting the output signal V2 of the second linear calibration circuit to the inputs of the first, second and third four fundamental rules operators;
means connecting the output signal V3 of the third linear calibration circuit to the inputs of the first, second and third four fundamental rules operators;
X1 being determined by the first four fundamental rules operator from the relationship:

$$X_1 = \frac{1}{\Delta}\left[\left(\frac{a_{22}a_{33}-a_{32}a_{23}}{K_1}\right) \times V_1 - \left(\frac{a_{12}a_{33}-a_{32}a_{13}}{K_2}\right) \times V_2 + \left(\frac{a_{12}a_{23}-a_{22}a_{13}}{K_3}\right) \times V_3\right]$$

$X_2$ being determined by the second four fundamental rules operator from the relationship:

$$X_2 = \frac{1}{\Delta}\left[\left(\frac{a_{21}a_{33}-a_{31}a_{23}}{K_1}\right) \times V_1 + \left(\frac{a_{11}a_{33}-a_{31}a_{13}}{K_2}\right) \times V_2 + \left(\frac{a_{11}a_{23}-a_{21}a_{13}}{K_3}\right) \times V_3\right]$$

$X_3$ being determined by the third four fundamental rules operator from the relationship:

$$X_3 = \frac{1}{\Delta}\left[\left(\frac{a_{21}a_{32}-a_{31}a_{22}}{K_1}\right) \times V_1 + \left(\frac{a_{11}a_{32}-a_{31}a_{12}}{K_2}\right) \times V_2 + \left(\frac{a_{11}a_{22}-a_{21}a_{12}}{K_3}\right) \times V_3\right]$$

wherein $$\Delta = \begin{vmatrix} a_{11} & a_{12} & a_{13} \\ a_{21} & a_{22} & a_{23} \\ a_{31} & a_{32} & a_{33} \end{vmatrix}$$

wherein $a_{11}, a_{12}, a_{13}, a_{21}, a_{22}, a_{23}, a_{31}, a_{32}$ and $a_{33}$ and $K_1$, $K_2$ and $K_3$ are constants and
wherein $V_1$, $V_2$ and $V_3$ are defined as follows:

$V_1 = K_1 (a_{11}X_1 + a_{12}X_2 + a_{13}X_3)$
$V_2 = K_2 (a_{21}X_1 + a_{22}X_2 + a_{23}X_3)$
$V_3 = K_3 (a_{31}X_1 + a_{32}X_2 + a_{33}X_3)$.

2. A radiometric analyzer for measuring the density, the sulfur content and the calorific value of a carbon, sulfur and hydrogen material by radiation comprising:
a $\gamma$ ray source for bombarding the material with $\gamma$ rays;
a $\gamma$ ray detector for receiving the $\gamma$ rays after bombardment with respect to the material;
a X-ray source for bombarding the material with X-rays;
a X-ray detector for receiving the X-rays after bombardment with respect to the material;
a thermal neutron source for bombarding the material with thermal neutrons;
a thermal neutron detector for receiving the thermal neutrons after bombardment with respect to the material;
a first four fundamental rules operator for generating an output indicative of the density of the material;
a second four fundamental rules operator for generating an output indicative of the sulfur content of the material;
a third four fundamental rules operator for generating an output indicative of the calorific value of the material;
means connecting the output signal of the $\gamma$ ray detector to the inputs of the first, second and third four fundamental rules operators;
means connecting the output signal of the X-ray detector to the inputs of the first, second and third four fundamental rules operators;
means connecting the output signal of the thermal neutron detector to the inputs of the first, second and third four fundamental rules operators;
the density being determined by the output $V'_1$ of the first four fundamental rules operator from the relationship $V'_1 = K''_1 (C + S + H) = K''_1 \rho$ ($\rho$ = density)

the sulfur content being determined by the output $V'_2$ of the second fundamental rules operator from the relationship $V'_2 = K''_2 S/(C + S + H) = K''_2 S/\rho$ (S/$\rho$ = sulfur content)

the calorific value being determined by the output $V'_2$ of the third four fundamental rules operator from the relationship $$V'_3 = K''_3 (k + lC + mS + nH) = K''_3 Q \quad (Q = \text{calorific value})$$

wherein $K''_1$, $K''_2$ and $K''_3$ are constants and wherein $$V'_1 = K'_1 (b_{11}V_1 + b_{12}V_2 + b_{13}V_3)$$

$$V'_2 = K'_2 \frac{b_{21}V_2 + b_{22}V_2 + b_{23}V_2}{V'_1}$$

$$V'_3 = K'_3 (b_{31}V_1 + b_{32}V_2 + b_{33}V_3 + b_0)$$

where $K'_1$, $K'_2$, $K'_3$, $b_{11}$, $b_{12}$, $b_{13}$, $b_{21}$, $b_{22}$, $b_{23}$, $b_{31}$, $b_{32}$, $b_{33}$ and $b_0$ are constants and wherein $$V_1 = K_1 (\mu_c C + \mu_s S + \mu_H H)$$
$$V_2 = K_2 (\mu'_c C + \mu'_s S + \mu'_H H)$$
$$V_3 = K_3 (\alpha C + \beta S + \gamma H)$$

and wherein $K_1$, $K_2$ and $K_3$ are constants.

* * * * *